US010828409B2

(12) United States Patent
Pilla et al.

(10) Patent No.: US 10,828,409 B2
(45) Date of Patent: Nov. 10, 2020

(54) NON-BLOOD CONTACTING MECHANICAL DEVICE THAT IMPROVES HEART FUNCTION AFTER INJURY

(71) Applicant: The Trustees of The University of Pennsylvania, Philadelphia, PA (US)

(72) Inventors: James J Pilla, Kennett Square, PA (US); Robert C Gorman, Lower Gwynedd, PA (US); Joseph H Gorman, III, Lower Gwynedd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/299,679

(22) Filed: Mar. 12, 2019

(65) Prior Publication Data

US 2019/0224395 A1    Jul. 25, 2019

Related U.S. Application Data

(63) Continuation of application No. 14/361,502, filed as application No. PCT/US2012/067410 on Nov. 30, 2012, now abandoned.

(Continued)

(51) Int. Cl.
*A61M 1/10* (2006.01)
*A61F 2/00* (2006.01)
*A61M 1/12* (2006.01)

(52) U.S. Cl.
CPC ........... *A61M 1/122* (2014.02); *A61M 1/1005* (2014.02); *A61M 1/106* (2013.01); *A61M 1/1008* (2014.02);

(Continued)

(58) Field of Classification Search
CPC ................ A61M 1/122; A61M 1/1068; A61M 2205/05; A61M 1/0209;

(Continued)

(56) References Cited

U.S. PATENT DOCUMENTS

| 4,192,293 A | 3/1980 | Asrican |
| 4,536,893 A | 8/1985 | Parravicini |

(Continued)

FOREIGN PATENT DOCUMENTS

| WO | 2012/075460 A2 | 6/2012 |
| WO | 2013/082505 A1 | 6/2013 |

OTHER PUBLICATIONS

International Application No. PCT/US2012/067410: International Search Report and Written Opinion dated Feb. 8, 2013, 15 pages.

(Continued)

*Primary Examiner* — Ann Schillinger
(74) *Attorney, Agent, or Firm* — BakerHostetler

(57) ABSTRACT

A method and device are provided for non-blood contact mechanically assisting an injured (e.g., infarcted) ventricle by coupling an inflatable bladder or other volume adjustable device to the injured ventricle and selectively inflating the bladder or increasing the size of the volume in systole to apply force against the injured ventricle and deflating the bladder or reducing the size of the volume in diastole to remove force against the injured ventricle. When no mechanical assistance is being provided to the injured ventricle, the inflatable bladder or volume adjustable device is preferably maintained at a predetermined pressure so as to selectively stiffen the injured tissue and alter ventricular geometry a desired amount. The method is implemented by a mechanical assist device including the volume adjustable device, a coupling means that couples the volume adjustable device to the injured ventricle, a pulsatile device that selec- (Continued)

tively increases and decreases the volume of the volume adjustable device, and a controller responsive to the pace of the heart and adapted to selectively change the size of the volume adjusting device in different modes of operation.

5 Claims, 14 Drawing Sheets

Related U.S. Application Data

(60) Provisional application No. 61/565,780, filed on Dec. 1, 2011.

(52) U.S. Cl.
CPC ......... *A61M 1/1068* (2013.01); *A61M 1/1086* (2013.01); *A61M 1/12* (2013.01)

(58) Field of Classification Search
CPC ...... A61M 2025/1095; A61M 2207/10; A61M 25/104; A61M 39/10
See application file for complete search history.

(56) References Cited

U.S. PATENT DOCUMENTS

| | | |
|---|---|---|
| 6,238,334 B1 | 5/2001 | Easterbrook et al. |
| 6,540,659 B1 | 4/2003 | Milbocker |
| 2005/0113632 A1 | 5/2005 | Ortiz et al. |
| 2006/0009676 A1 | 1/2006 | Melvin |
| 2006/0129025 A1 | 6/2006 | Levine et al. |
| 2007/0073218 A1 | 3/2007 | Lau et al. |
| 2008/0021260 A1 | 1/2008 | Criscione et al. |
| 2008/0064917 A1 | 3/2008 | Bar et al. |
| 2011/0021864 A1 | 1/2011 | Criscione et al. |

OTHER PUBLICATIONS

George et al., "Surgical Treatment of Advanced Heart Failure: Alternatives to Heart Transplantation and Mechanical Circulatory Assist Devices", Progress in Cardiovascular Diseases, 2011, 54, 115-131.

European application No. 12883992.1: European Search Report dated Aug. 3, 2015, 6 pages.

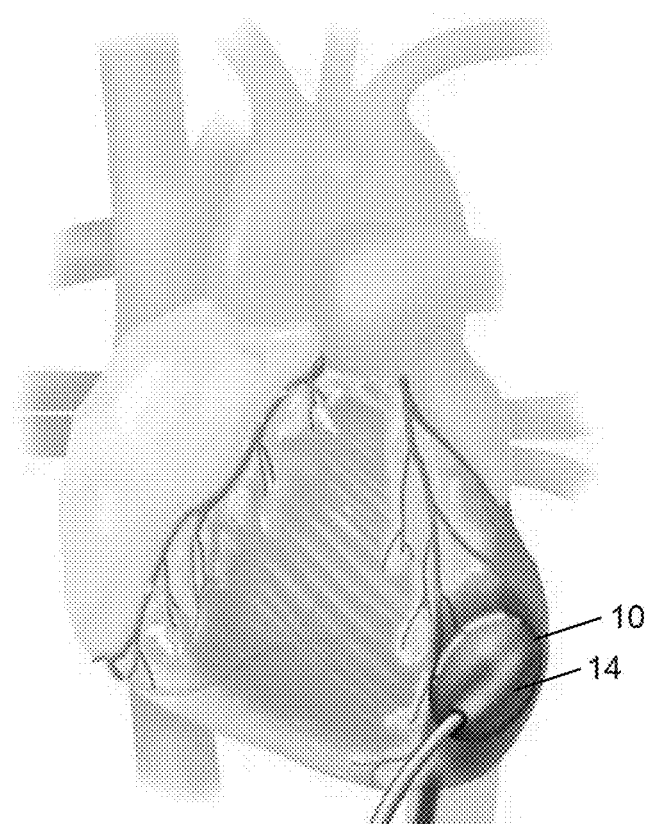
Fig. 1A
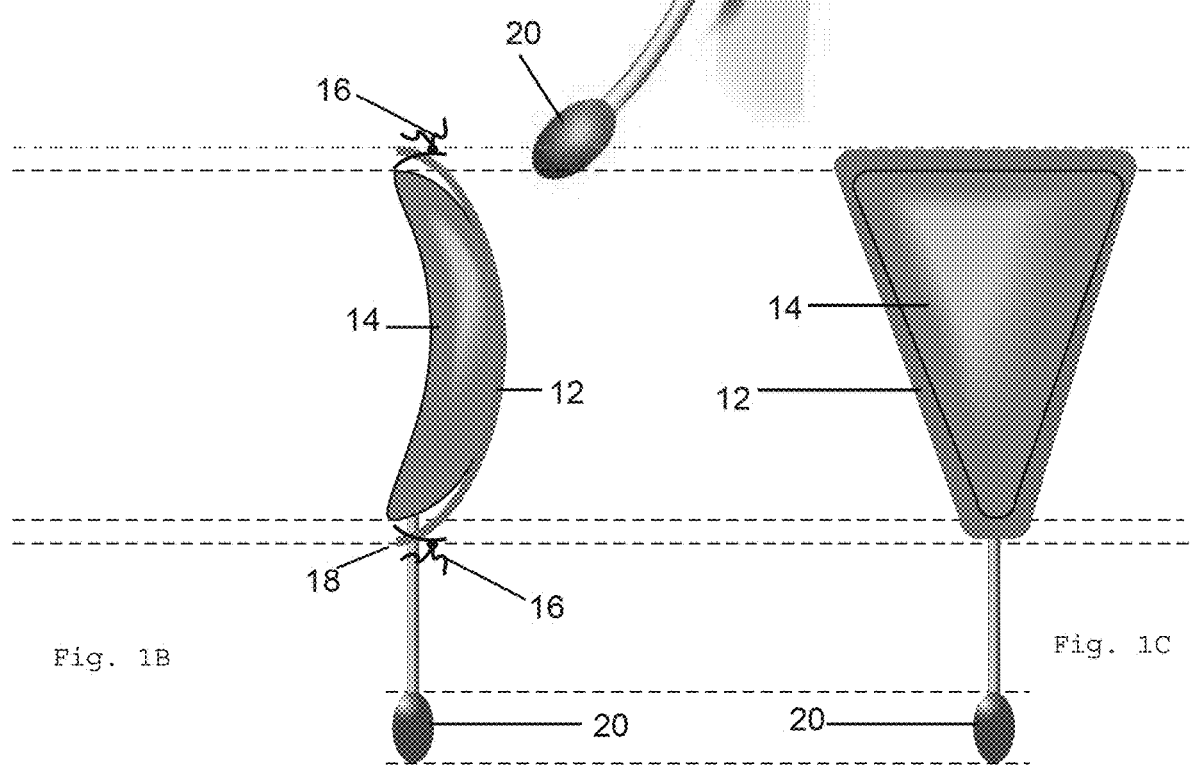
Fig. 1B
Fig. 1C

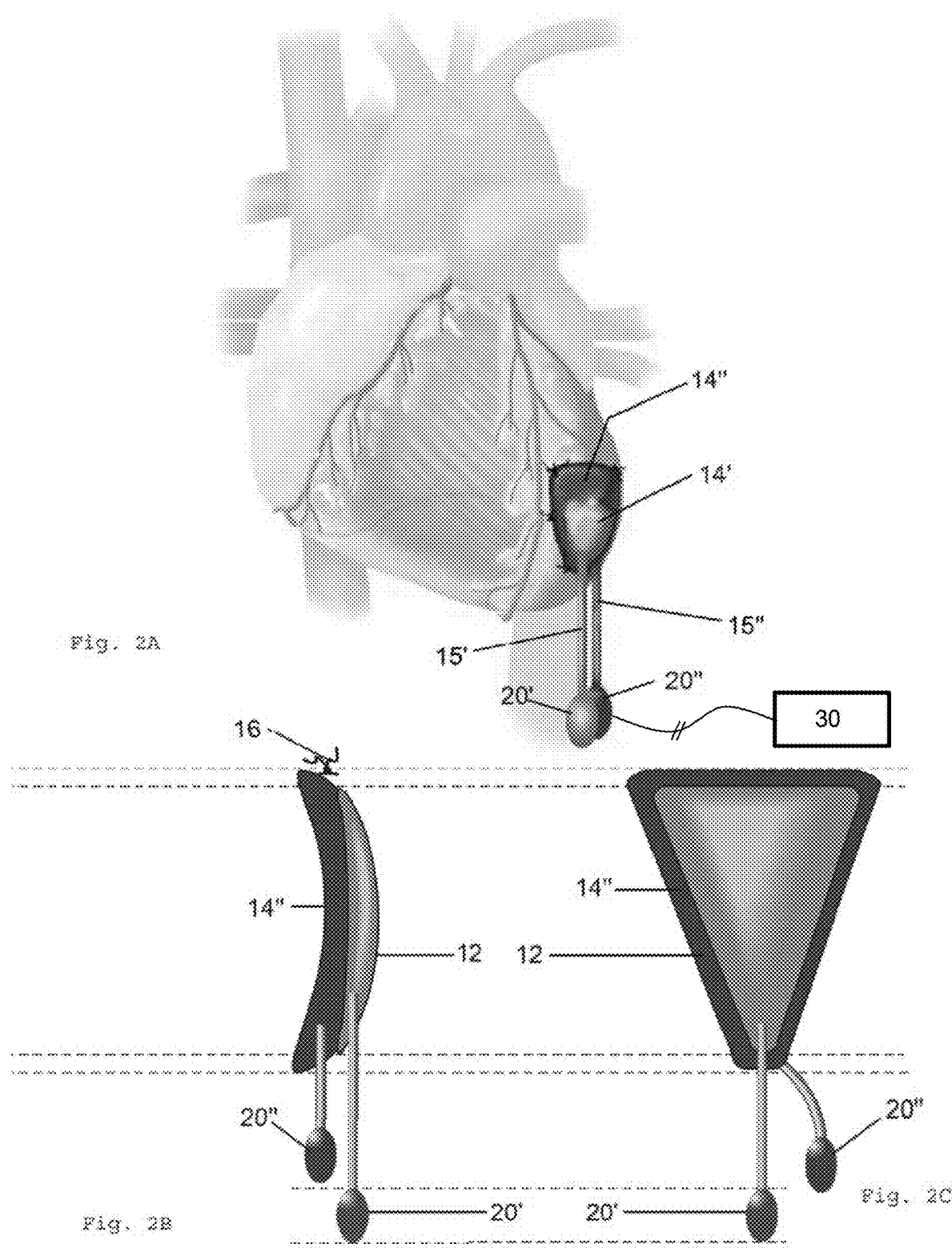

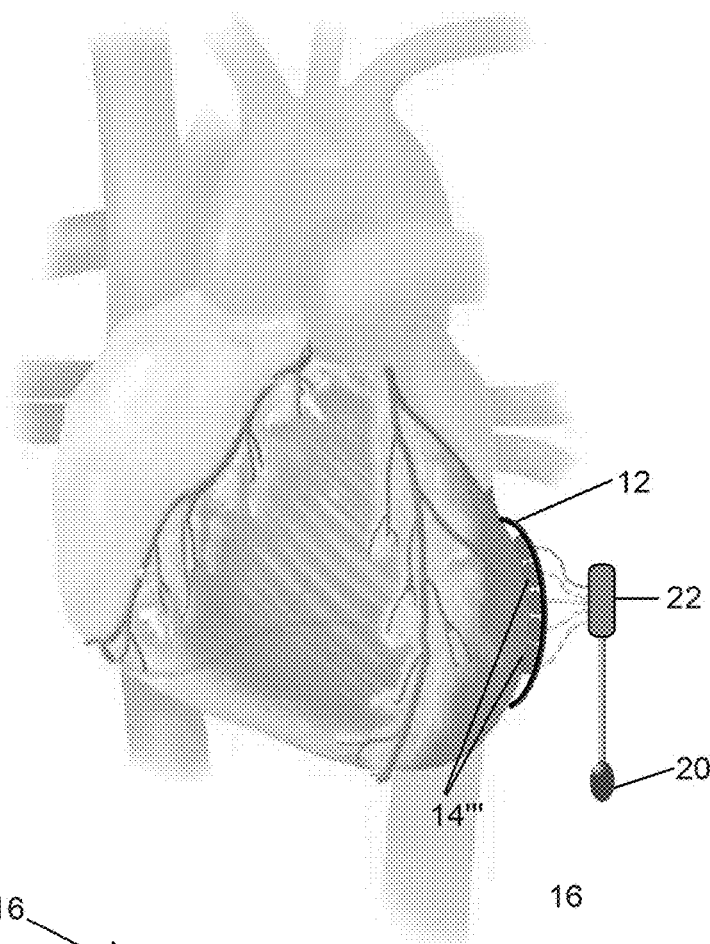
Fig. 3A
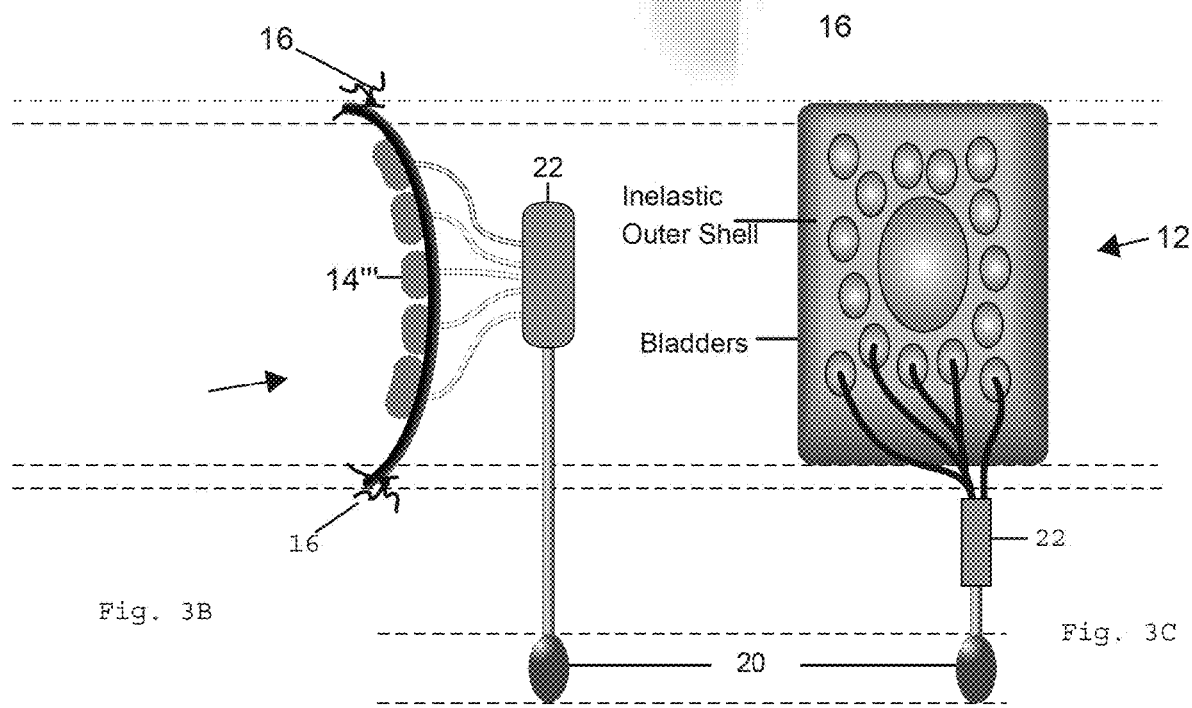
Fig. 3B
Fig. 3C

Fig. 8A
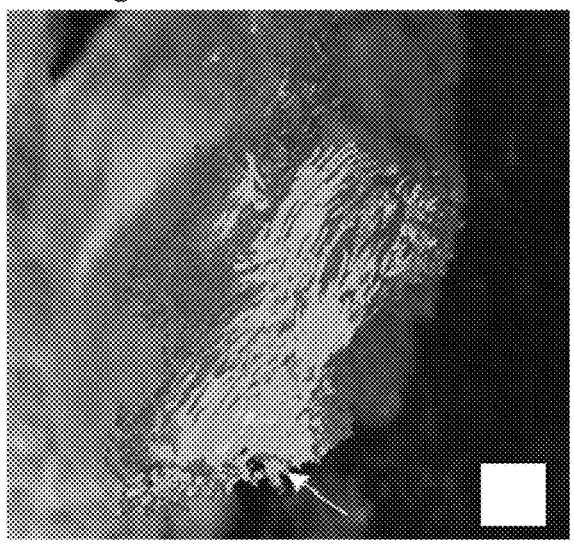
Fig. 8B
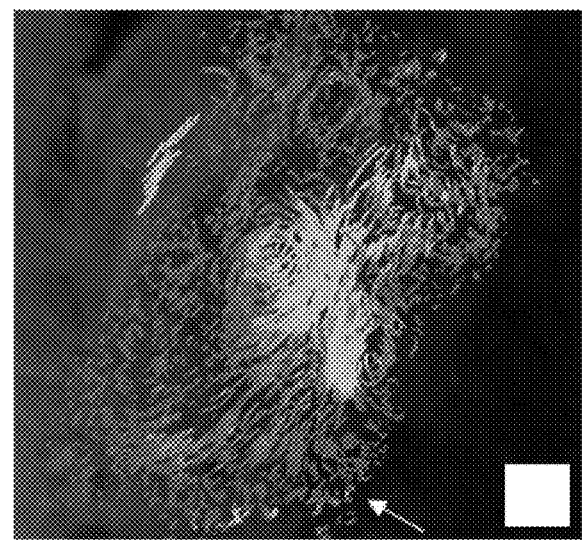
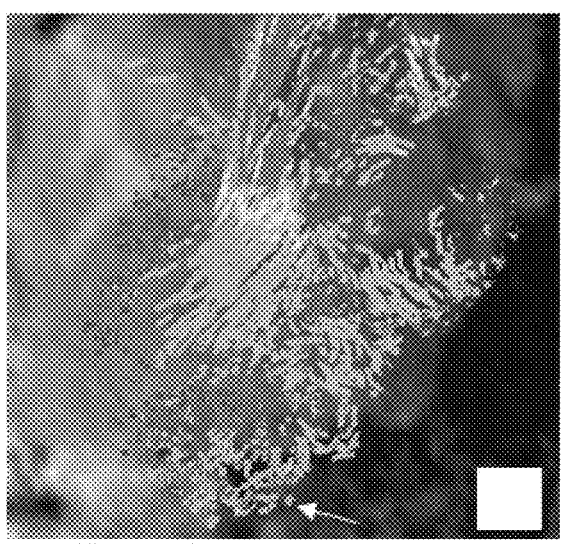
Fig. 8C
Fig. 8D
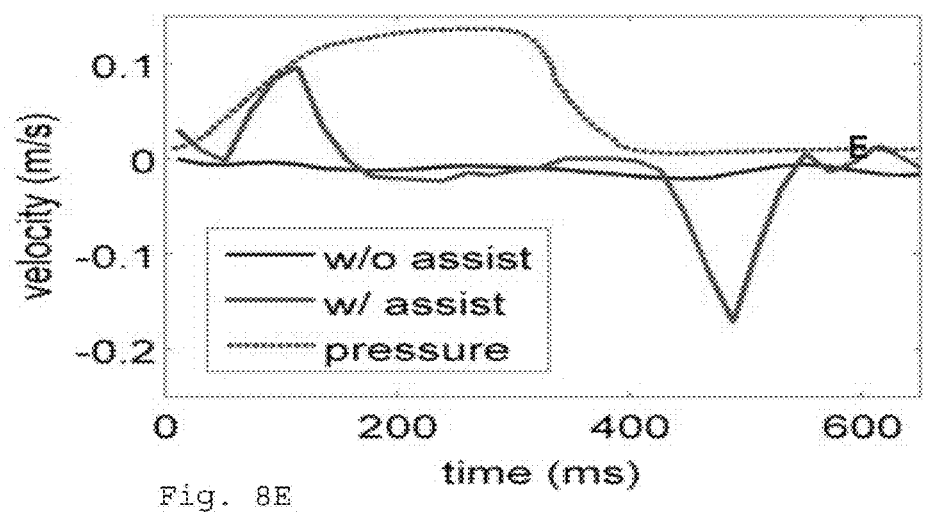
Fig. 8E Cardiac gating signal Device pressure

NON-BLOOD CONTACTING MECHANICAL DEVICE THAT IMPROVES HEART FUNCTION AFTER INJURY

CROSS-REFERENCE TO RELATED APPLICATIONS

This application is a continuation of U.S. Ser. No. 14/361,502, filed May 29, 2014, which is the National Stage of International Application No. PCT/US2012/067410, filed Nov. 30, 2012, which claims the benefit of U.S. Provisional Application No. 61/565,780, filed Dec. 1, 2011, the entire contents of each of which are incorporated herein by reference for any and all purposes.

TECHNICAL FIELD

The invention relates to a mechanical device that is affixed to a portion of the ventricular epicardial surface to improve the function of the heart after it has experienced an injury such as a myocardial infarction.

BACKGROUND

Myocardial infarction as well as other injuries and diseases lead to structural changes in the heart that result in the alteration of infarct (injured tissue) material properties and ventricular geometry. Following the injury, necrotic myocardium and the normal extracellular matrix are replaced by a disarranged collagen network, which ultimately leads to scar formation. These histologic and cellular changes that occur directly alter the mechanical stiffness of the injured myocardial tissue and surrounding non-injured myocardium (border zone). Theoretical left ventricular (LV) modeling and experimental data from animal experiments have demonstrated that material properties of the injured area and its geometry have a profound effect on global and regional ventricular function that occur immediately after the injury and progress in severity over time.

Progressive impairment in cardiac function after injury is due not only to a loss of contracting myocardium but also to the short-term and long-term mechanical and biologic effects of the injury on the normally perfused myocardium. While injured tissue material properties (elastance) have been theoretically predicted to have significant effects on cardiac performance, surprisingly little is known about the changes in material properties that occur as the injury heals. It has been hypothesized that increased material elastance (reduction in stiffness), which has been demonstrated to occur during injury healing and maturation, contributes to the progressive loss of global cardiac function experienced by many patients after myocardial infarction (MI).

Ischemic cardiomyopathy is associated with a multitude of chronic changes to the geometry, function, and biomechanics of the failing ventricle. Infarct expansion results in progressively enlarging adynamic or hypokinetic myocardium which can significantly alter the fluid dynamics within the ventricle. Early studies utilizing conductance catheter-based LV pressure-volume loops have shown that infarction raises the "zero-pressure volume" within the ventricle (i.e., $V_0$)—increasing the amount of functional dead space. This dead space permits an increasing portion of the blood in the LV to reside in an area that has impaired contractile function while better functioning portions of the heart remain relatively unloaded. Newer evidence from velocity-encoded 3D MRI also supports the formation of abnormal flow patterns within the left ventricle as the heart remodels—resulting in an increasing amount of retained blood within the ventricle (i.e., residual volume). These abnormal flow patterns can reduce the hearts contractile efficiency, impair mitral valve function and increase the risk of blood clot formation in the heart. The inventors have hypothesized that restoring or normalizing physiologic flow patterns may improve left ventricular mechanics and efficiency, improve mitral valve function, and reduce the risk of blood clot embolization. While many invasive therapies have been described for the treatment of ischemic heart failure (see, e.g., George et al., Prog. Cardiovasc. Disease (2011), Vol. 54, pp. 115-131), few have been designed to alter left ventricular residual volume (or $V_0$) or LV blood flow patterns by directly changing the mechanics and geometry of the pathologic myocardium.

The increased elastance (reduced stiffness) in the injured area of the heart results in increased mechanical stress in the injured region. This increase in stress alters how the injured area heals. The type and amount of collagen that is produced during injury healing is negatively influenced by elevated mechanical stress in the injured area. The inventors have demonstrated that limiting mechanical stress in the injured area improves healing and increases stiffness in the injured area.

Currently, the inventors are aware of no methods to variably adjust regional infarct elastance, LV geometry, or to perform regional assistance to the infarcted (injured) region of the heart. Injectable materials and cell therapies have been directed at this clinical problem but cannot be easily optimized in a patient specific manner or provide active assistance in addition to infarct stiffening. These techniques also cannot influence material properties and ventricular geometry to the extent that the proposed invention would be capable of accomplishing.

It is thus desired to stiffen the injured tissue (infarct) in-vivo to improve function and mitigate remodeling and to develop an in-vivo method of altering injured tissue (infarct) elastance and geometry and to provide assistance in synchrony with remote myocardial contraction. The present invention addresses these needs in the art.

SUMMARY

The invention addresses the above-mentioned needs in the art by providing an epicardial assist device that can actively assist injured myocardium in synchrony with remote myocardial contraction and improve injured tissue (infarct) elastance and ventricular residual volume and geometry in response to remote myocardial contraction. The injured tissue (infarct) is stiffened in-vivo by coupling the injured (infarct) region to an elastic fluid fill chamber, such as an inflatable bladder, and then varying the volume in the fluid fill chamber to alter the injured tissue material properties. The device so configured has been shown to provide diminished ventricular remodeling and improved LV function as evidenced by the improvement in end-systolic volume and ejection fraction.

In an exemplary embodiment, the invention provides a mechanical device that is affixed to a portion of the ventricular epicardial surface to improve the function of the heart after it has experienced an injury such as a myocardial infarction. The device can be operated in active mode, passive mode or both simultaneously. In passive mode, the device can variably stiffen the injured tissue (infarct) to variably alter the ventricular geometry and eliminate the volume of blood contained by the dyskinetic injured region in both diastole and systole. In diastole, the passive device acts to shift the blood volume to the more normally functioning contractile regions of the ventricle that are remote from the injury. This improves contractility in these remote regions based on Starlings Law of the Heart. In systole, the passive device prevents the dyskinetic region from acting as a capacitor (energy sink) that absorbs contractile energy that would otherwise go into driving blood out the aortic valve during the injection phase of the cardiac cycle. On the other hand, the active mode produces two effects in systole: 1) direct assistance to the injured tissue (infarct) region augmenting systolic ejection (the device imparts energy directly to the circulation) and 2) further reduction of the capacitor (energy sink) effect that is produced by the dyskinetic injured region. During diastole in active mode, the device promotes ventricular filling by a suction effect. This increased ventricular performance is again based on Starlings Law of the Heart.

Methods of mechanically assisting an injured heart ventricle in accordance with exemplary embodiments of the invention include the steps of coupling an elastic fluid fill chamber, such as an inflatable bladder, to the injured ventricle and selectively adjusting the chamber volume by, for example, inflating the bladder in systole to apply force against the injured ventricle and by, for example, deflating the bladder in diastole to remove force against the injured ventricle. In a static mode of operation, the pressure of the fluid fill chamber is maintained at a predetermined pressure so as to selectively stiffen the injured ventricle a desired amount. In static mode operation, the fluid fill chamber variably alters a geometry of the injured ventricle to a pre-injury shape by eliminating a cavity volume of the ventricle bounded by the injured ventricle tissue. The inflatable fill volume also redirects blood volume from a non-contractile injured region of the ventricle to a contractile remote region of the ventricle.

The mechanical assist device for providing active assistance to an injured ventricle in accordance with the inventive method includes in an exemplary embodiment an elastic fill chamber such as an inflatable bladder, means for coupling the fill chamber to the injured ventricle, means for adjusting the volume in the fill chamber, such as a pneumatic unit that selectively inflates and deflates a bladder, and a control unit responsive to the pace of the heart and adapted to selectively increase the volume of the fill chamber (e.g., inflate the bladder) in systole to apply force against the injured ventricle and to decrease the volume of the fill chamber (e.g., deflate the bladder) in diastole to remove force against the injured ventricle. In an exemplary embodiment, the means for selectively adjusting the volume of the fill chamber includes a controller responsive to the pace of the heart and adapted to selectively expand the volume of the fill chamber in systole to apply force against the injured ventricle and to selectively reduce the volume of the fill chamber in diastole to remove force against the injured ventricle. In an embodiment in which the fill chamber is a bladder, a fluid fill port selectively fills the bladder with fluid under control of a pulsatile device responsive to the controller. In a static mode, the fill chamber is maintained at a predetermined volume to selectively stiffen the injured ventricle and/or to alter the ventricle geometry a desired amount.

In exemplary embodiments, the fill chamber is adapted to be implanted in a patient on epicardial tissue so as not to contact blood being pumped by the patient's heart. The fill chamber also may have an inelastic outer shell to direct force from the fill chamber towards the ventricle. The fill chamber is coupled to the epicardial tissue using any of a number of suitable means such as sutures.

The fill chamber may include a single bladder, a bladder having a first portion for accepting a first fluid and a second portion for accepting a second fluid provided by first and second fill ports, or a plurality of bladders adapted to accept fluid from a plurality of fluid fill ports. The fluid may be a gas or a liquid.

In exemplary embodiments, the mechanical assist device operates in a plurality of operational modes. For example, the means for selectively adjusting the volume of the fill chamber is adapted to operate in a static mode where the fill chamber is affixed over the injured ventricle and filled with fluid to a predetermined volume, a synchronous dynamic mode that times expansion and reduction of the fill volume with the cardiac cycle, and/or an asynchronous dynamic mode in which an amplitude, frequency, and/or duration of the adjustment of the volume of the fill chamber is adjusted independent of the cardiac cycle.

In alternative embodiments, the fill chamber may be replaced by a solid material configured to change size of the ventricle when affixed to the injured tissue so as not to contact blood being pumped by the patient's heart. This material is coupled to the heart adjacent the injured tissue and functions to selectively stiffen the injured tissue and/or to alter ventricle geometry a desired amount over time. The solid material may be individualized for a patient by appropriate selection of the position, size, and volume of the solid material.

BRIEF DESCRIPTION OF THE DRAWINGS

The various novel aspects of the invention will be apparent from the following detailed description of the invention taken in conjunction with the accompanying drawings, of which:

FIG. 1 illustrates an epicardial surface showing an infarct area, a single bladder design for a fluid fill chamber, and an outer shell that may be a polypropylene mesh or an inelastic outer shell that restrains the bladder against the infarct region in accordance with the invention. FIG. 1A is a perspective view, FIG. 1B is a side view, and FIG. 1C is a rear view.

FIG. 2 illustrates an epicardial surface showing an infarct area, a dual bladder design for a fluid fill chamber, and an outer shell that may be a polypropylene mesh or an inelastic outer shell that restrains the bladders against the infarct region in accordance with the invention. FIG. 2A is a perspective view, FIG. 2B is a side view, and FIG. 2C is a rear view.

FIGS. 3A-3C illustrate a multi-bladder design for a fluid fill chamber and an outer shell that may be a polypropylene mesh or an inelastic outer shell that restrains the bladders against the infarct region in accordance with the invention. FIG. 3A is a rear view, FIG. 3B is a side view, and FIG. 3C is a rear view.

FIG. 8 illustrates the effect of synchronized dynamic mode on regional flow when an assist device is placed at the arrow position whereby diastolic flow velocity increases with device activation at FIG. 8A compared to non-assist at FIG. 8B. Flow in systole is also increased with activation at FIG. 8C compared to unassisted at FIG. 8. The activation of the assist device produces positive flow in systole propelling blood out of the heart while rapid deflation of the device during diastolic filling (FIG. 8A and FIG. 8B) creates diastole negative flow (suction effect on nearby blood) which augments filling as shown at FIG. 8, resulting in flow velocities over 150 cm/s towards the ventricular wall, while rapid inflation of the device during early systole (FIG. 8C and FIG. 8D) forces volume away from the infarct at approximately 100 cm/s, and, in doing so, eliminates intraventricular volume surrounded by adynamic myocardium.

DETAILED DESCRIPTION OF ILLUSTRATIVE EMBODIMENTS

The invention will be described in detail below with reference to FIGS. 1-14. Those skilled in the art will appreciate that the description given herein with respect to those figures is for exemplary purposes only and is not intended in any way to limit the scope of the invention. All questions regarding the scope of the invention may be resolved by referring to the appended claims.

Figure 13:
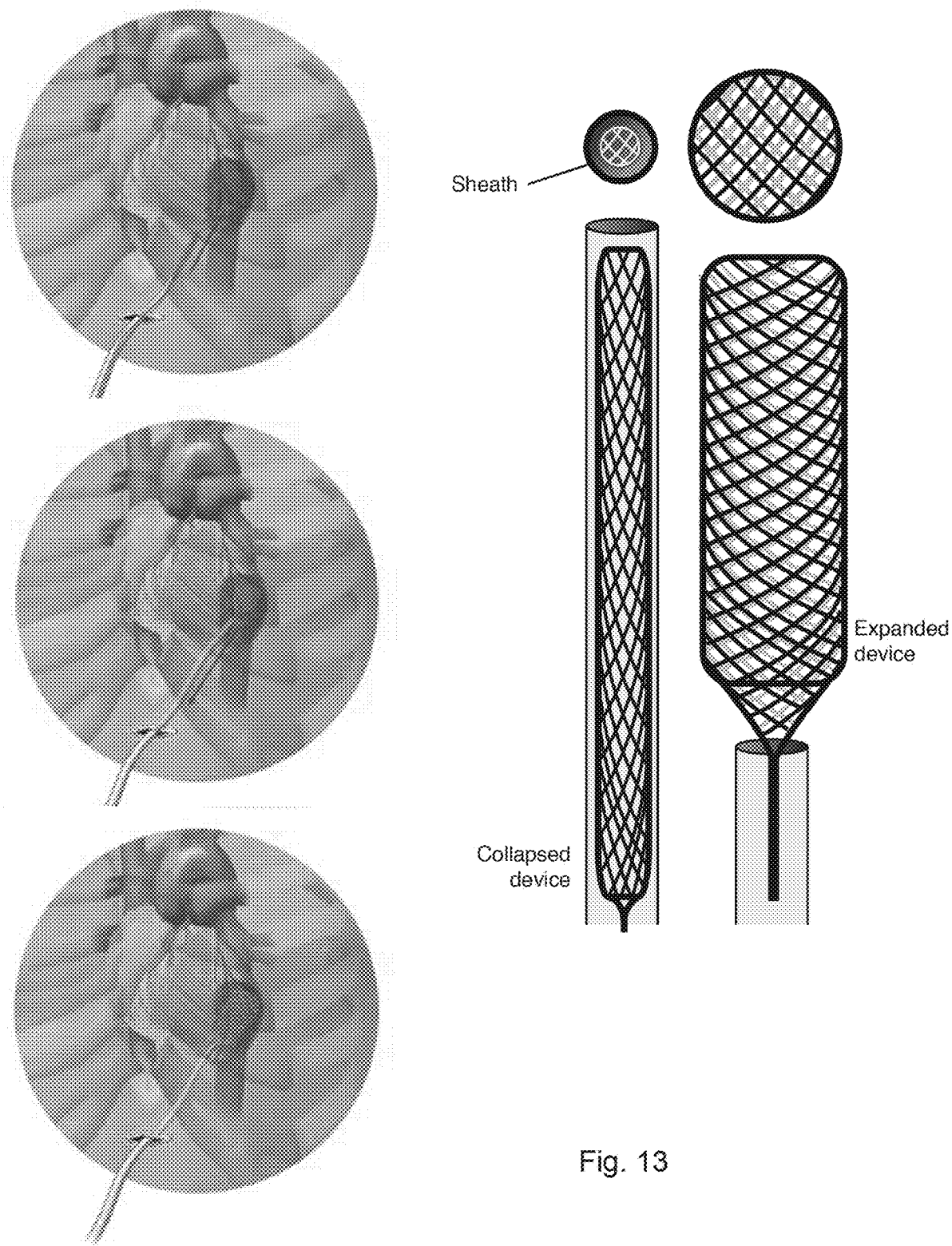
FIG. 13 illustrates placement of the assist device on the infarct via transcutaneous techniques where the assist device is in the form of a wire mesh that is collapsed for insertion into a delivery sheath and is placed via a subxiphoid approach.

In order to variably adjust the injured tissue (infarct) elastance and LV geometry in-vivo, the device 10 of FIGS. 1A-1C has been developed that couples the injured tissue (e.g. infarct) to a coupling means 12 such as an external mesh forming a composite material or an inelastic outer shell made of, for example, ePTFE or Dacron. The device 10 of FIGS. 1A-1C couples the injured tissue to the external mesh or inelastic outer shell 12 using a fluid fill chamber (e.g., bladder) 14 made of, for example, silicone, PET, urethane, or nylon, and placed between the injured tissue area and the external polypropylene mesh or inelastic outer shell 12. The external mesh or inelastic outer shell 12 is held against the injured tissue (infarct) region by suturing the external mesh or inelastic outer shell 12 to the epicardial surface of the heart using, for example, sutures 16 and cell adhesion promoters 18. In addition, an implantable (subcutaneous) fill port may be exteriorized that allows the fluid fill chamber 14 to be connected to an external pneumatic or other volume adjustment device for adjustment of the volume of the fluid fill chamber and thus injured tissue stiffness. Of course, mesh or an inelastic outer shell 12 is not necessary. Any coupling means that may couple, attach, or fix the fluid fill volume to a specified epicardial region is all that is needed. The coupling means may be inelastic, partially elastic, or directionally elastic in order to customize the treatment. Also, the device does not necessarily need to include a fluid filled bladder. A solid (e.g., egg-shaped) material configured to change LV size when affixed to the heart in the area of injury could achieve the intended result. Preoperative stress modeling based on MRI, echocardiography and/or other imaging tests could be used to design the solid object based on an individual patient's heart shape. A self-expanding wire mesh device constructed of stainless steel or nitinol could also be designed to achieve a similar result. FIG. 13 illustrates an assist device is in the form of a wire mesh.

In exemplary embodiments, the fluid fill chamber 14 includes one or more inflatable bladders 14. The inflatable bladder 14 can consist of a single bladder 14 with one filling chamber as shown in FIGS. 1A-1C. A single fill port 20 is connected to the bladder 14 to adjust its size by adding or removing of fluid or gas. The mesh or inelastic outer shell 12 is attached to the bladder 14 and is used for attachment and as a buttress to direct the force inward towards the epicardium.

Alternatively, the fluid fill chamber 14 may include a dual bladder configuration including a bladder with a partition creating two independent sections 14' and 14" as shown in FIG. 2. One section 14' is filled with fluid and is used in the static mode to stiffen the heart and to adjust geometry. An independent fill port 20' is attached to the static bladder section 14' to adjust volume. The other section 14" is filled with a gas and is used in the dynamic mode to assist the heart under the control of a pulsatile device 30. It has an independent fill port 20" to provide cyclic volume changes. Attached to the outer surface of the dual bladder is a mesh or an inelastic shell 12 to direct force inward.

To allow for in situ adjustment, a multiple bladder device system has been developed. It consists of multiple small and large bladders 14''' arranged in the same plane (FIGS. 3A and 3B). Each bladder 14''' has its own fill port 20 that is connected to a manifold 22. Removing bladders 14''' and sealing the port 20 to that specific bladder 14''' only can adjust the size of the device 10. Bladders 14''' of various sizes, shapes, and number can be used in the device 10 of FIGS. 3A and 3B.

The device 10 can function in at least three different modes: static, synchronous dynamic, and asynchronous dynamic. It can operate in a single mode or any combination of the three simultaneously or consecutively depending on need.

Figure 4B:
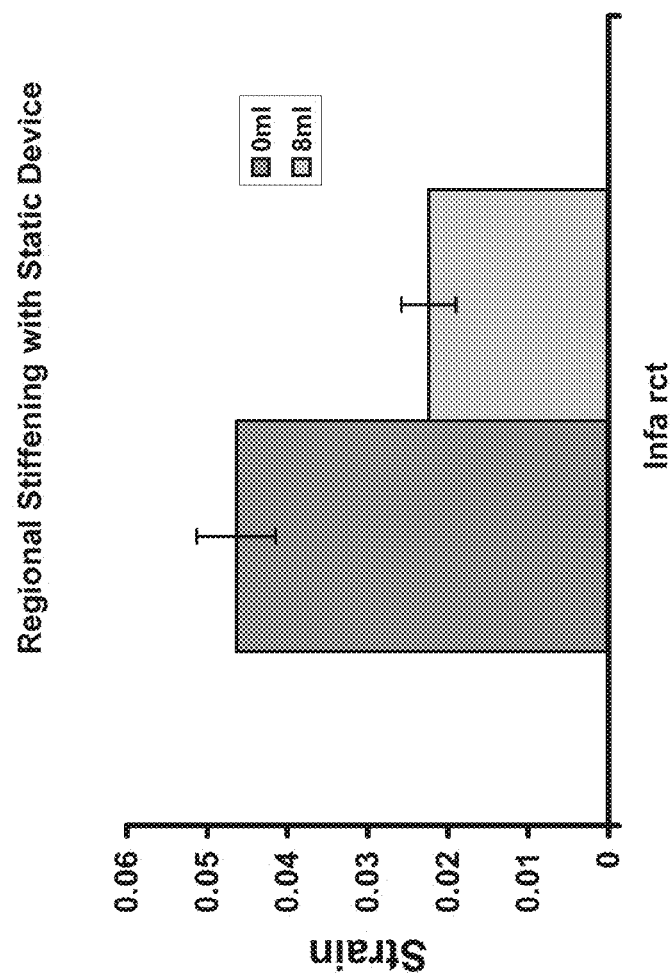
FIG. 4B is a graph showing that infarct strain significantly decreases in device static mode indicating that the device has stiffened the region, resulting in less stretch and dyskinetic motion.
Figure 4A:
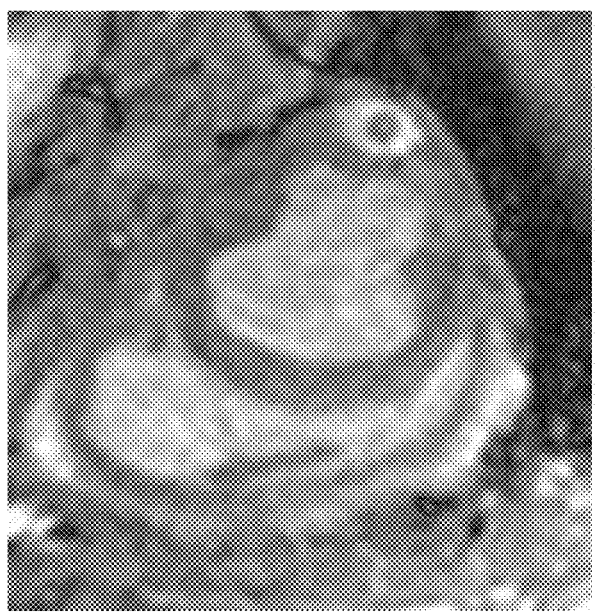
FIG. 4A illustrates an MRI image of the heart in device static mode where the device is affixed over the infarct region and filled with fluid.
Figure 5:
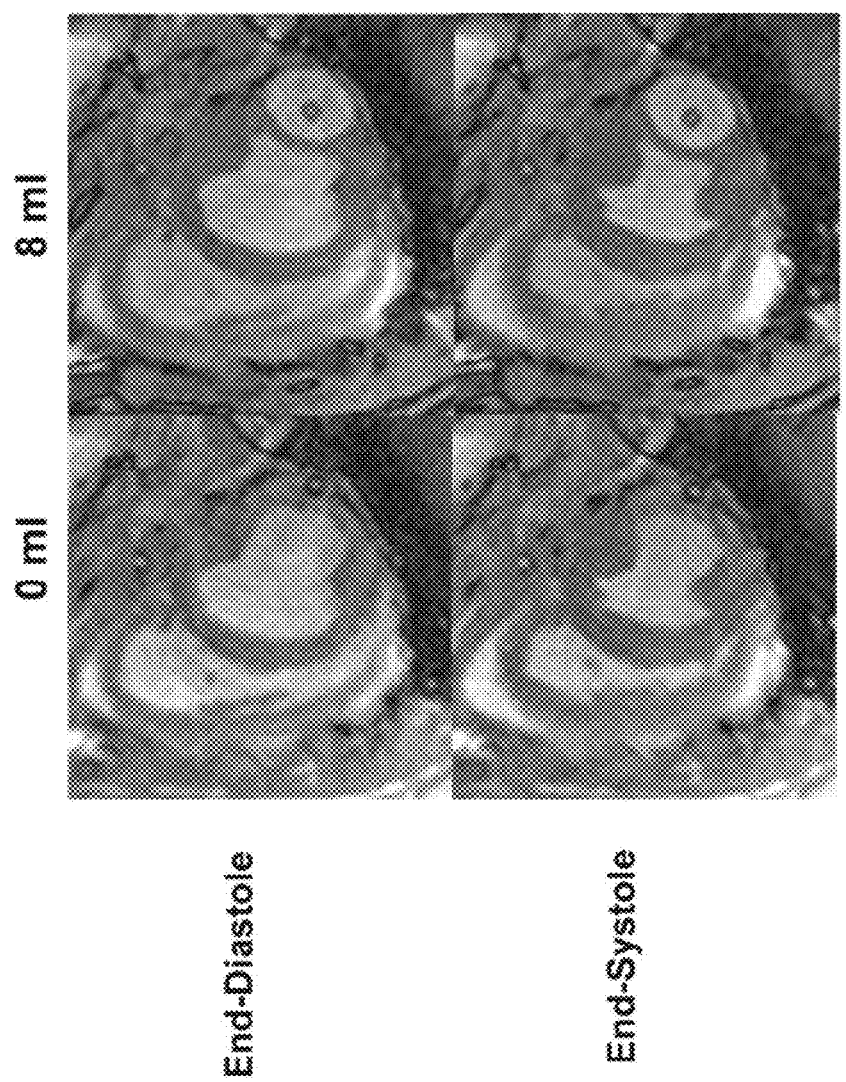
FIG. 5 illustrates ultrasound images of the heart in device static mode following an infarct at end-diastole and end-systole to illustrate that the geometry of the left ventricle becomes abnormal (0 ml) due to altered regional material properties and contractility and that filling the device restores the left ventricular geometry to a more normal shape and dimensions (8 ml).

Static mode includes the device volume remaining constant at a predetermined value and only being altered when required to adjust effect on cardiac function. This mode is used to stiffen the region under the device decreasing regional strain (FIG. 4). FIG. 4A illustrates an image of the heart in device static mode where the device is affixed over the infarct region and filled with fluid. FIG. 4B is a graph showing that infarct strain significantly decreases in device static mode indicating that the device has stiffened the region, resulting in less stretch and dyskinetic motion. Regional and global geometry is altered from an abnormal shape to a more normal shape using this mode (FIG. 5). FIG. 5 illustrates images of the heart in device static mode following an infarct at end-diastole and end-systole to illustrate that the geometry of the left ventricle becomes abnormal (0 ml) due to altered regional material properties and contractility and that filling the device restores the left ventricular geometry to a more normal shape and dimensions (8 ml) (see description of FIG. 6 below). Also, volume is shifted from dead space bounded by the abnormal geometry to the remote regions increasing loading and strain. The static mode also effects wound healing by decreasing static and cyclic strain. Large cyclic or static strain has been shown to decrease fibroblast stimulation to produce collagen resulting in a more compliant infarct.

Synchronous dynamic mode, on the other hand, includes filling the device 10 in a manner that is cyclically synchronized to the native heart contraction (see description of FIG. 7 below). This mode provides partial assist without blood contact moving the blood out of the device-applied region during systole and augmenting filling during diastole (see description of FIG. 8 below). This mode adds energy to the system and decreases the workload of the heart.

Figure 9A:
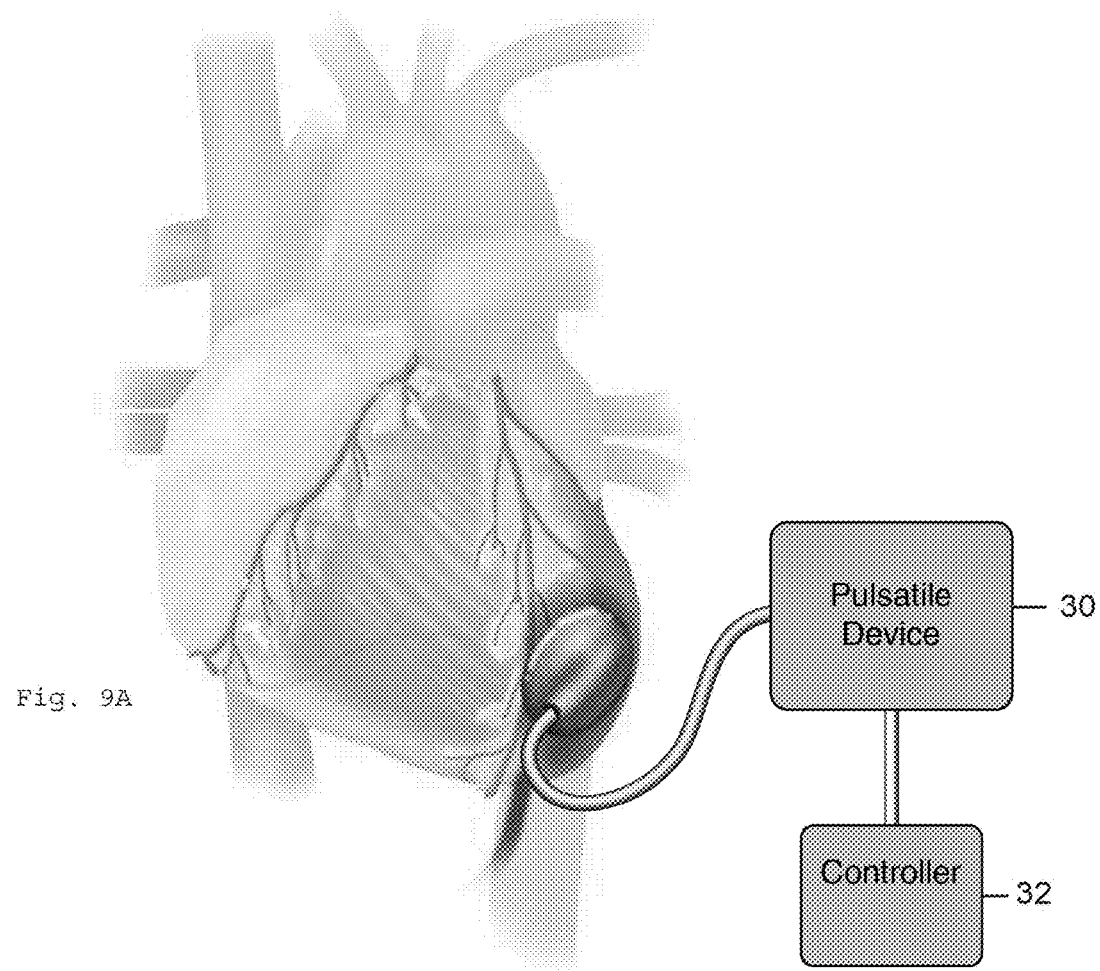
FIG. 9A illustrates an embodiment for implementing an asynchronous dynamic mode using a pulsatile device responsive to a programmed controller. The amplitude, frequency, and duration of the pulsation of the device can be adjusted as desired and is not synchronized to the cardiac cycle as illustrated in FIG. 9B.
Figure 9B:
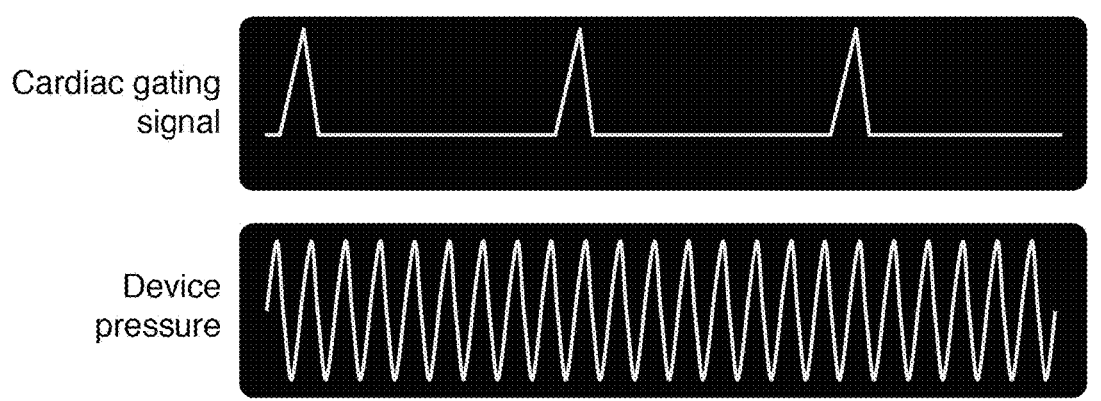

Asynchronous dynamic mode provides non-heart synchronized volume pulsations at various amplitudes, frequencies, and durations (FIG. 9). FIG. 9A illustrates an embodiment for implementing an asynchronous dynamic mode using a pulsatile device responsive to a programmed controller. The amplitude, frequency, and duration of the pulsation of the device can be adjusted as desired and is not synchronized to the cardiac cycle as illustrated in FIG. 9B. This mode cyclically alters strain in both the device-applied region and the remote non-device contact regions. Strain amplitude, frequency, and duration alter wound healing and material properties changing the regional stiffness of the heart. For example, high frequency, low amplitude adjustments that are not synchronized with the heart beat may affect the healing process by slightly moving the heart tissue and potentially improving tissue characteristics through slight movement of the otherwise restrained infarcted tissue. Fibroblasts have been shown to respond to cyclic low amplitude strain by increasing collagen production and tissue tensile strength.

The device of FIG. 1 was assessed using a swine infarct model. A 20% posterolateral infarct was created and the device was placed over the infarct region. Five days post infarction the animal was imaged using a 3T MRI scanner (Siemens TIM Trio). Left ventricular volume and strain were measured at baseline and at a bladder volume of 8 ml using a 3D SPAMM tagged pulse sequence. Image analysis was performed using an optical flow method (OFM). Langranian strain results were determined from which the 3D principal strains where calculated. Left ventricular volumes were measured from long-axis 3D TrueFISP images.

Figures 6A, 6B:
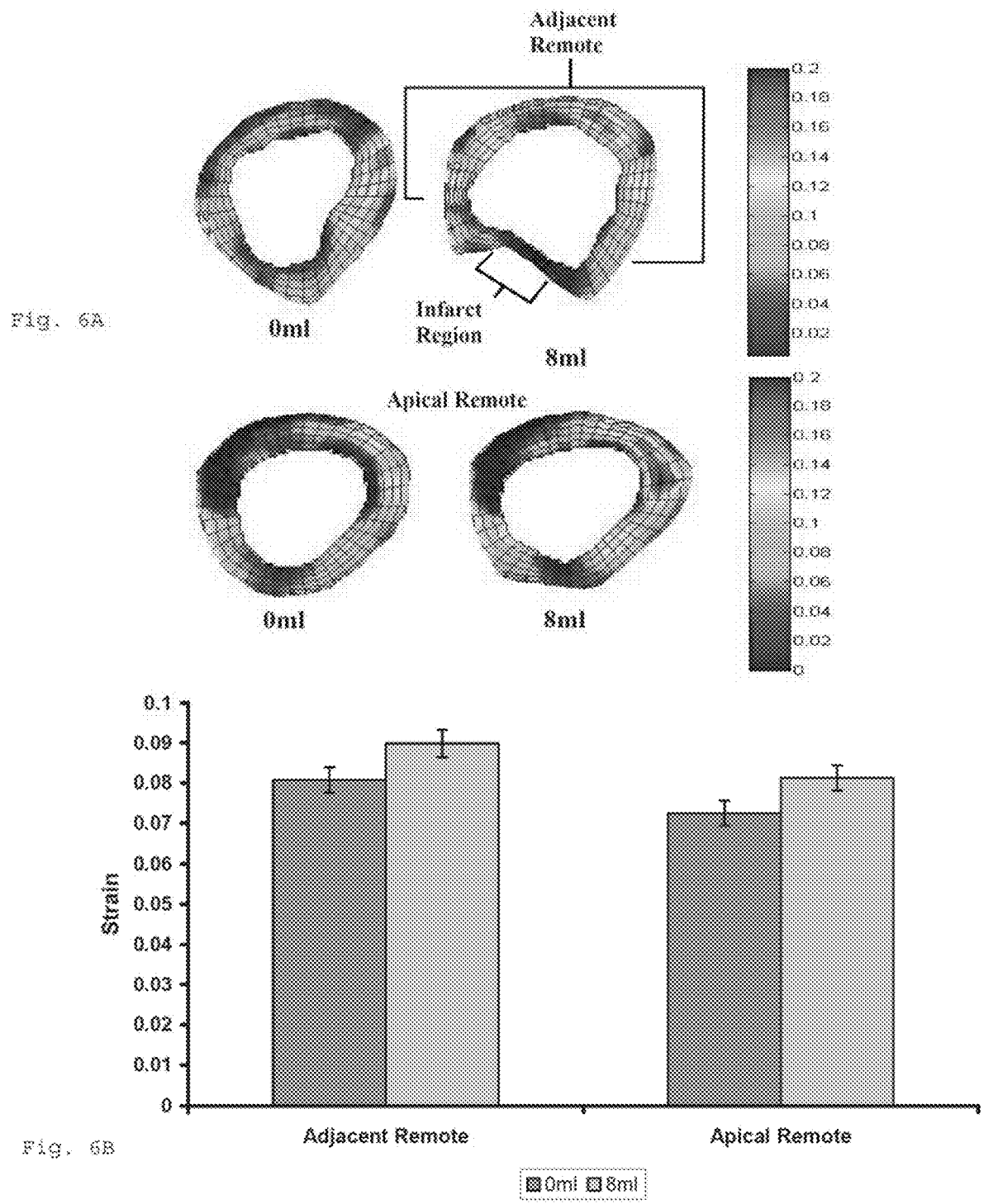
FIG. 6A illustrates maximal principal strain and LV deformation in an infarcted animal at bladder volumes of 0 mL and 8 mL for a slice adjacent to the infarct and an apical slice remote from the infarct.
FIG. 6B is a graph showing that in device static mode filling the device shifts the volume from the dead space to the remote myocardium, increasing loading and strain production.

FIG. 6A illustrates maximal principal strain and LV deformation in an infarcted animal at bladder volumes of 0 mL and 8 mL for a slice adjacent to the infarct and an apical slice remote from the infarct. In the figure, adjacent remote refers to the non-infarcted region in the same short access slice, while apical remote refers to a region at the apex of the heart that is furthest from the infarct. FIG. 6B is a graph showing that in device static mode filling the device shifts the volume from the dead space to the remote myocardium, increasing loading and strain production. It will be appreciated by those skilled in the art that FIG. 6A illustrates short axis slices demonstrating maximum principal stain vector magnitude. Maximum principal strain in the remote region adjacent to the infarct improved (0.08 (0 ml) versus 0.095 (8 ml)) when the bladder 14 was inflated from 0 ml to 8 ml. Infarct principal strain decreased with bladder inflation (0.04 (0 ml) versus 0.02 (8 ml)) indicating infarct stiffening. Remote apical strain also improved with inflation (0.07 (0 ml) versus 0.085 (8 ml)). The change in strain and the observed alteration of the LV geometry with bladder inflation is confirmation of the shift volume from the akinetic infarct region to the contractile remote region. Left ventricular volumes at 0 ml were 91.6 mL (EDV—end diastolic volume) and 59.7 mL (ESV—end systolic volume), 31.9 mL (SV—stroke volume) and 34.8% (EF—ejection fraction). At 8 mL, left ventricular volumes were as follows: 87.7 mL (EDV), 46.7 mL (ESV), 41.0 mL (SV) and 46.7% (EF). The device 10 was shown to acutely increase infarct stiffness in a graded fashion and to reduce infarct dyskinetic movement. An improved contractile function and less LV remodeling out to 4 weeks after infarction was observed.

When the device 10 was deflated in these experiments 4 weeks after infarction it was found that the infarct remained stiff; there was no bulging of the infarct as was seen in the untreated controls. This finding demonstrated that the infarct had healed differently as a result of the 4 weeks of restraint. This is analogous to a bone healing while it is rendered immobile by a cast or splint. Reduction in injury stress improved healing and caused the infarct to be permanently stiffened by the temporary restraint.

In this large animal model, total elastance of the infarct area was altered by coupling the infarct to an external mesh 12 via an inflatable bladder 14. The induced increased elastance was transmitted over the infarct and border zone region resulting in altered maximal principal strain magnitude and direction. Altering strain direction in the border zone from stretch to thickening combine with the decreased infarct stretch was found to have a positive effect on attenuating myocardial remodeling and infarct expansion.

Figures 7A, 7B:
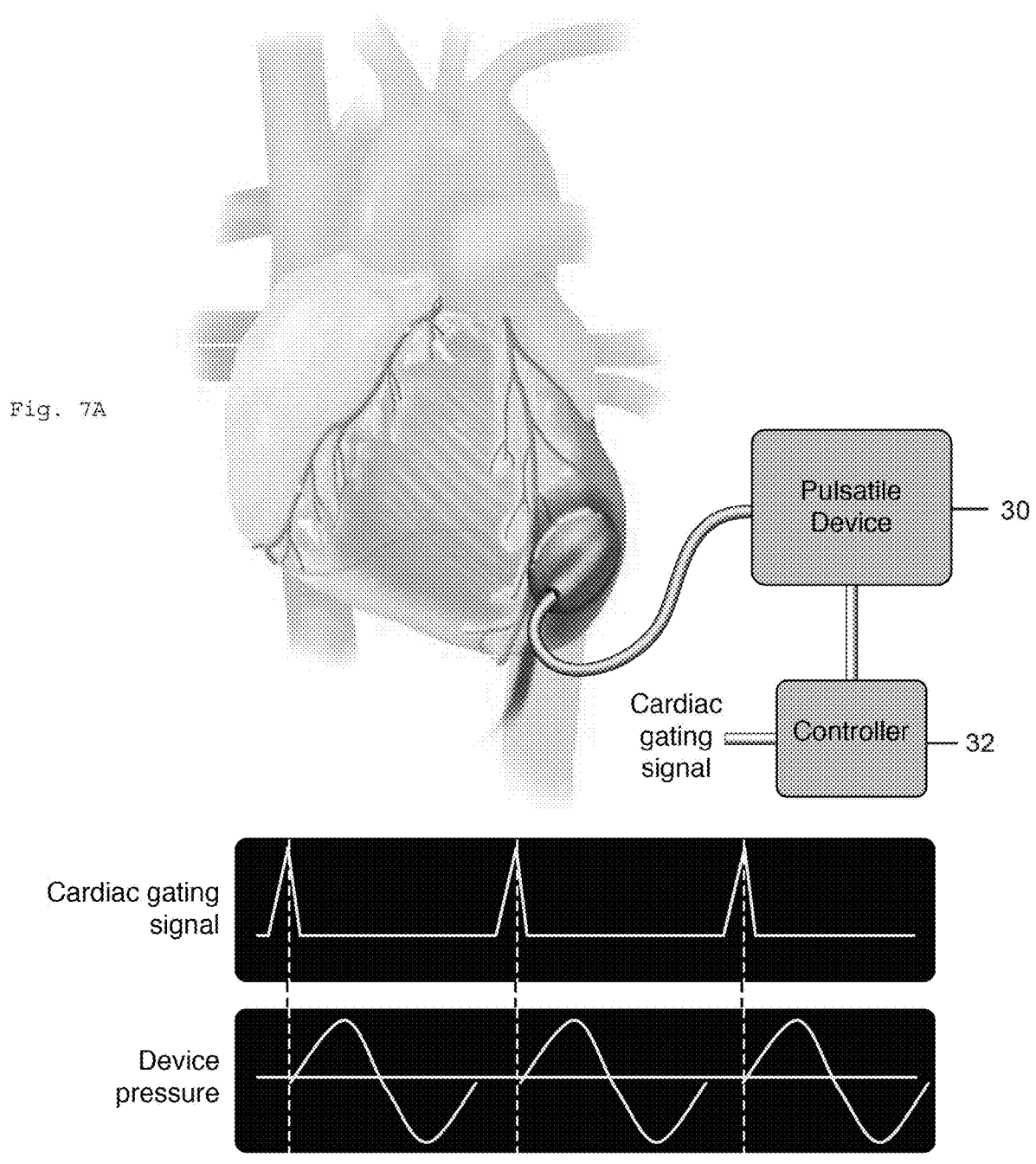
FIG. 7A illustrates an embodiment for implementing a synchronous dynamic mode using a pulsatile device responsive to a programmed controller. The pulsation of the device is timed to the measured cardiac cycle using a cardiac gating signal as illustrated in FIG. 7B.

To determine the effect of the device 10 of FIG. 1 with cyclic stiffening on LV function, a group of animals received a posterolateral infarct with the device 10 placed at the time of infarct creation. An exteriorized port 20 connected the bladder 14 to a pneumatic pulsatile device 30 controlled by a controller 32 during data and image collection as shown in FIG. 7, where FIG. 7A illustrates an embodiment for implementing a synchronous dynamic mode using a pulsatile device responsive to a programmed controller. As shown, the pneumatic pulsatile device 30 is responsive an ECG input that provides a cardiac gated signal (FIG. 7B) indicative of the atrial pace of the heart and that is ported to the pneumatic pulsatile device 30 by controller 32 as a gating trigger for bladder inflation and deflation during the heart cycle.

In a passive (static) mode, the bladder is inflated by a pneumatic drive unit to an optimal level for the individual patient and varied over time in accordance with the desired stiffness of the infarct region. However, in accordance with an exemplary embodiment, the device may be selectively inflated/deflated by the pneumatic drive device in response to outputs from controller 32 at the respective portions of the cardiac cycle (FIG. 7B) so as to provide active assistance during systole and diastole by producing local deformation of the infarct region via a pneumatic pump of the pulsatile device 30 synchronized to the cardiac cycle. The controller 32 and pneumatic drive unit of the pulsatile device 30 are powered by a suitable power supply (not shown). Thus, the device of FIG. 7 can be used to both passively stiffen the infarct and to produce active assistance.

The device 10 of FIG. 7 has passive and dynamic assist modes. In the passive mode (i.e., when no inflating/deflating of the bladder 14 in response to the atrial pace is conducted), the bladder 14 is filled to an optimal level as determined by ejection fraction and stroke volume. The bladder 14 is continually adjusted to maintain optimal performance by adding or removing volume as needed. The dynamic mode, on the other hand, provides direct assistance to the left ventricle. The assistance is directed to the dyskinetic infarct region, which amplifies the effect of the assist by moving blood out of the dyskinetic region during systole and allowing filling during diastole. This aspect not only provides assistance but also decreases left ventricular stress and workload. The synchronous dynamic mode is synchronized to the cardiac cycle and timing and can be adjusted to optimize left ventricular function. The fill pattern can also be modified to alter the rate and duration of inflation and deflation. The device 10 can also function in dual passive and dynamic assist mode. This mode varies the passive and dynamic components of the assist to optimally improve left ventricular function.

The device of FIG. 7 was tested on five Yorkshire swine that underwent direct ligation of the circumflex artery via thoracotomy to create a posterolateral myocardial infarction (MI). Twelve weeks post-infarct, a custom-made inflatable neoprene bladder was placed on the transmurally infarcted epicardial surface. LV pressures were continuously recorded using a Millar pressure transducer catheter (Millar Instruments, Houston, Tex.). A pressure-gated, synchronous pulsation device 10 was connected to the epicardial bladder and positioned outside the magnetic field. The bladder 14 was then inflated during systole and deflated during diastole via rapidly exchanged helium gas. Using a 3.0 T Siemens MAGNETOM Trio A Tim, the animals then underwent cardiac and respiratory gated cardiac MRI. LV volumes with the device 10 off (deflated) and during active assistance were obtained using a 2D SPGR sequence with the following parameters: TR/TE/FA=24.2 ms/2.4 ms/150, BW=400, FOV=300 mm×243 mm, Matrix=192×156, slice thickness=4 mm, Ave.=2, cardiac phases=16-20 depending on heart rate. LV volumes and ejection fraction (EF) were then calculated using ImageJ image analysis software. LV function was compared using a paired t-test. 4D phase contrast MRI also was safely performed during active mechanical assistance and with no assistance. 4D phase contrast pulse sequence parameters used for this acquisition were as follows: Venc=75 cm/s, Spatial Resolution=2×2×2 mm, Temporal Resolution=20.8 ms.

When compared with the unassisted state, flow patterns near the assist device 10 were found to be significantly altered in both systole and diastole. During early diastolic filling, rapid deflation of the device created a suction effect on nearby blood—resulting in flow velocities over 150 cm/s towards the ventricular wall. FIG. 8 illustrates the effect of synchronized dynamic mode on regional flow when an assist device 10 is placed at the arrow position whereby diastolic flow velocity increases with device activation at (A) compared to non-assist at (B). Flow in systole is also increased with activation at (C) compared to unassisted at (D). The activation of the assist device 10 produces positive flow in systole propelling blood out of the heart while rapid deflation of the device 10 during diastolic filling (A and B) creates diastole negative flow (suction effect on nearby blood) which augments filling as shown at (E)—resulting in flow velocities over 150 cm/s towards the ventricular wall, while rapid inflation of the device 10 during early systole (C and D) forces volume away from the infarct at approximately 100 cm/s, and, in doing so, eliminates intraventricular volume surrounded by adynamic myocardium.

Figure 14B:
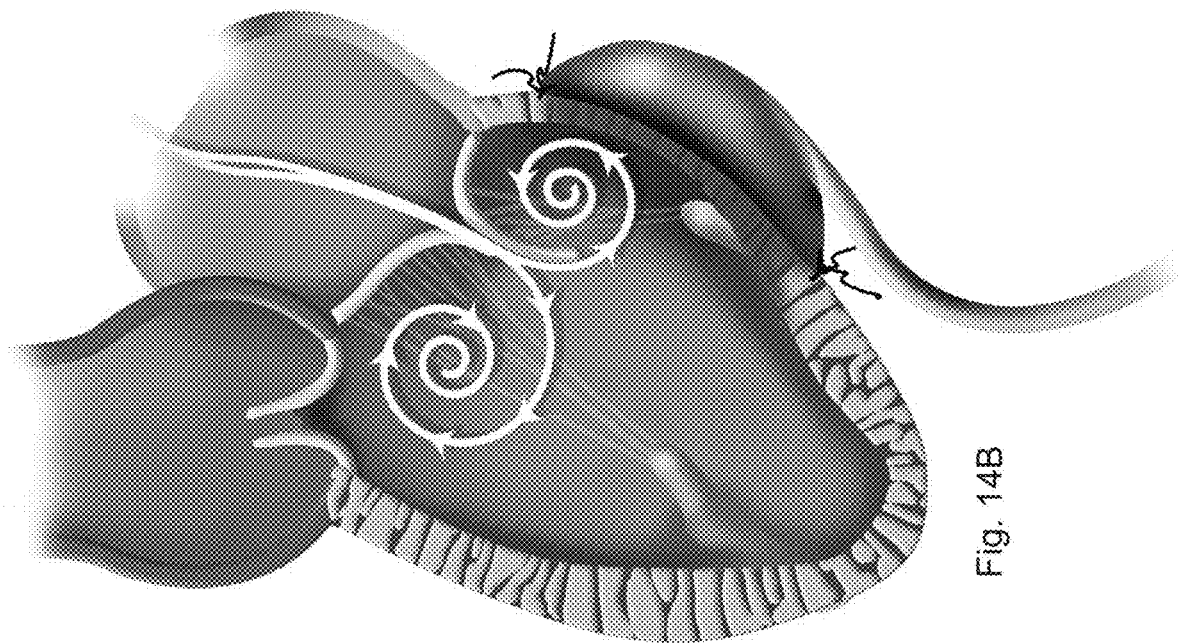
FIGS. 14A and 14B illustrate the influence of the assist device on MR and LV vortex formation without assist at FIG. 14A and with assist at FIG. 14B.
Figure 14A:
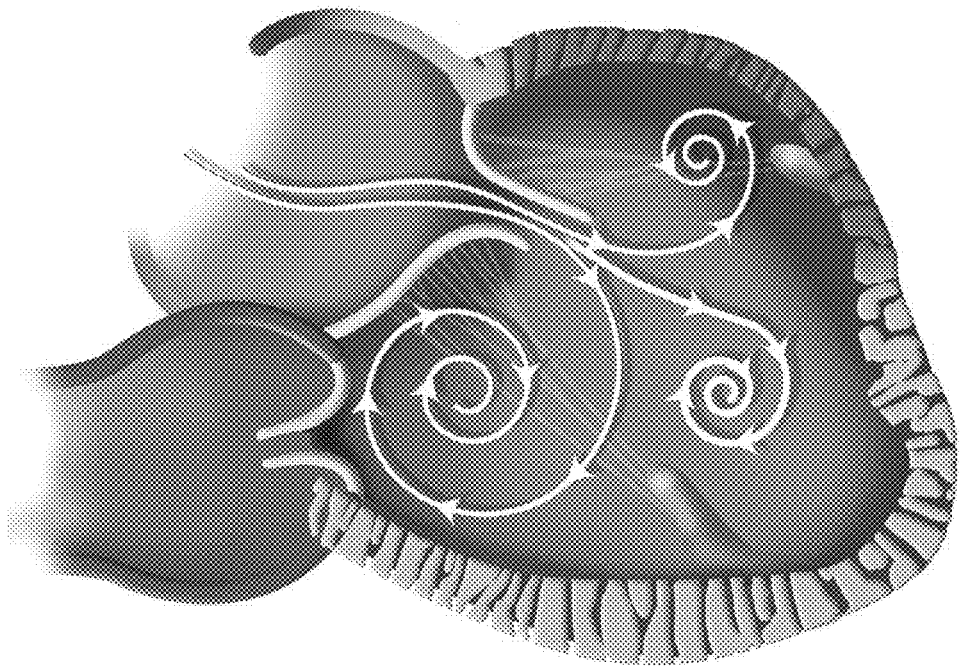

These findings are in stark comparison to the unassisted ventricle—where minimal flow is identified in this region throughout the cardiac cycle as shown in the flow profiles of FIG. 8E. As the normal heart fills in diastole, vortices are formed behind the anterior and posterior mitral valve leaflets that help the valve to close. FIG. 14 illustrates the influence of the assist device on MR and LV vortex formation without assist at (A) and with assist at (B). The formation of these vortices is disturbed in the heart after infarction. Application of the restraint device 10 normalizes LV vortex formation and improves mitral valve closure especially in patients with mitral regurgitation that results from LV remodeling (known as functional mitral regurgitation).

While being assisted, the subject's MRI showed a clear concave deformity over the infarct area during systole, while diastolic geometry was largely preserved. When compared with non-assist, synchronized epicardial assistance on the infarct area improved EF dramatically (34.1±7.8% vs. 22.8±9.2%, p=0.02). Similarly, end systolic volume was significantly decreased in the assisted group (75.7±25.7 ml vs. 90.3 ml±28.8, p=0.01). Stroke volume also increased in the assisted group and showed a trend towards significance (37.4±4.4 ml vs. 25.0±6.7 ml, p=0.08). End diastolic volume did not change between treatments (113±24.8 ml vs. 115.4±22.1 ml, p=0.5).

The device of FIG. 7 in operation has thus shown that chronic adverse ventricular remodeling as a result of myocardial infarction decreases the functional (ejected) volume within the ventricle while increasing the residual volume and $V_0$. The mechanical assist device 10 of the invention has been used to dramatically increase ventricular flow near the infarcted myocardium during both systole and diastole. By rapidly inflating the device in systole, the ventricular geometry not only changes, but blood volume with a predisposition to stagnation is forcibly moved from the adynamic endocardial surface to the contractile remote regions. During diastole, rapid deflation results in negative pressure being applied to the epicardial surface—which in turn augments local diastolic filling and flow via a suction effect. The mechanical assist device 10 of the invention thus enables one to change and quantify the flow profile of the failing ventricle which may in turn provide improved efficiency and function as well as improved mitral valve function and a reduction in the risk of thromboembolism (thrombus formation occurs in areas of stagnant blood flow).

The assist device 10 of the invention increases efficiency of the injured heart in both active and passive modes. A positive effect for the heart is produced that requires little energy consumption by the device 10. Increased efficiency is not dependent on energy transfer from the device 10 to the heart and circulation which is how conventional ventricular assist devices work. Moreover, by shifting blood in diastole to the uninjured (or less injured) areas, the contractile reserve of these areas may be "recruited" based on Starlings Law of the Heart. Also, the capacitor (energy sink) contribution of the infarct during systole may be eliminated. The passive mode can do that and it is potentiated in the active mode. Moreover, the active mode adds energy directly to the circulation by forcing blood through the aortic valve during systole and augments filling of the heart during diastole.

Patient Specific Application

Figure 10:
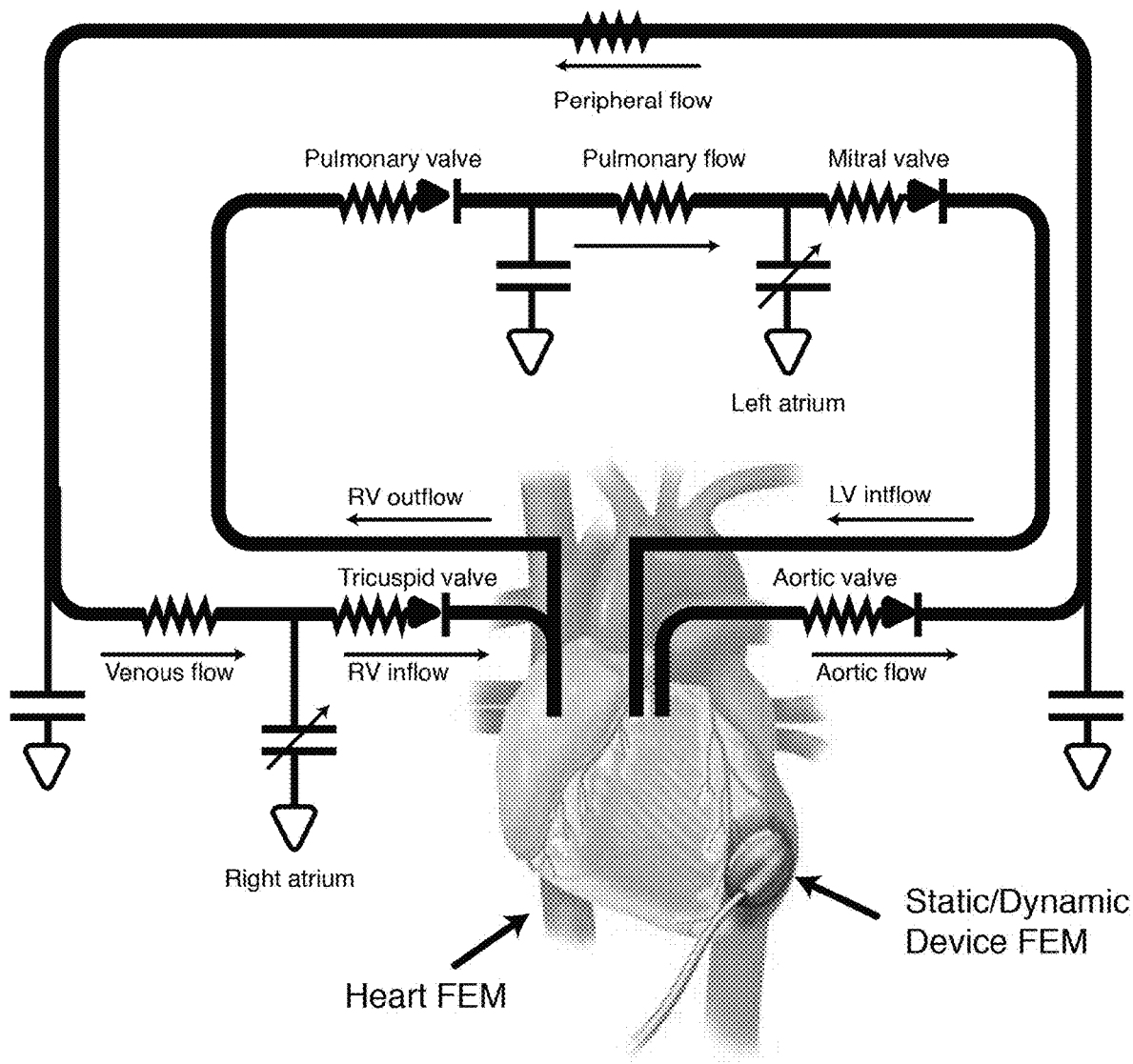
FIG. 10 illustrates a model used to optimize the static and dynamic device for specific patient application. The device is modeled using finite element analysis and is coupled to the heart finite element model (FEM) and lumped parameter model of the cardiovascular system.

The device sizing, mode, function, and position may be determined specifically for each individual patient. FIG. 10 illustrates a model used to optimize the static device for specific patient application. The device is modeled using finite element analysis and is coupled to the heart FEM and lumped parameter model of the cardiovascular system. Those skilled in the art will appreciate that modeling the device 10 combined with a coupled lumped parameter model of the cardiovascular system and finite element model (FEM) of the heart will determine optimal device parameters. In the static device mode, the optimal position, size and volume is determined from the model based on input data from MRI and ultrasound. The model optimizes the static mode using the following parameters: end-diastolic volume, end-systolic volume, stroke volume, ejection fraction, stroke work, $O_2$ consumption, aortic flow, aortic pressure, mitral valve regurgitation, regional strain, and regional stress. The parameter model may also be used to identify strain patterns that are unique to the patient and then simulating those patterns for application to the patient in ways that could, for example, improve the positioning and control of a mitral valve prosthetic device so as to reduce leaflet chordae tension.

The dynamic mode optimization includes contraction timing, amplitude, and waveform. Optimization is performed using a model of the dynamic device coupled to the cardiovascular model described above with respect to FIG. 10. The model will optimize dynamic function using the parameters presented above.

Wound Healing

The assist device 10 also can promote wound healing by altering strain and stress on the heart, by redistributing blood to improve efficiency, and preventing pooled blood. Mechanically stiffening the infarct using the static device over time decreases stress and strain promoting wound healing and permanent alteration of the infarct material properties. Cyclic strain in the device asynchronous mode also can promote wound healing. Mechanical cyclic strain stimulates the wound healing process resulting altered material properties.

Dynamic Contraction Methods

Though the embodiments above primarily discuss use of an inflatable bladder as the elastic fluid fill chamber 14, other types of devices may be used. For example, dynamic contraction of the device 10 can be performed by mechanical, chemical, and cellular methods. Mechanical methods include pneumatic, electromagnetic, and shape memory alloys. Chemical methods include, for example, carbon nanotubes. Cellular methods include the use of in vivo native muscle to power the device 10 and ex vivo implanted muscle.

Device Implantation

Those skilled in the art will also appreciate that the successful application of the assist device to the heart requires 5 distinct steps:

1. Access (Surgical, Minimal Invasive Surgery (MIS), Percutaneous)
2. Heart Stabilization
3. Device Delivery
4. Device Fixation
5. Device Optimization Each of these steps will be described in turn.

1. Access

Figure 11:
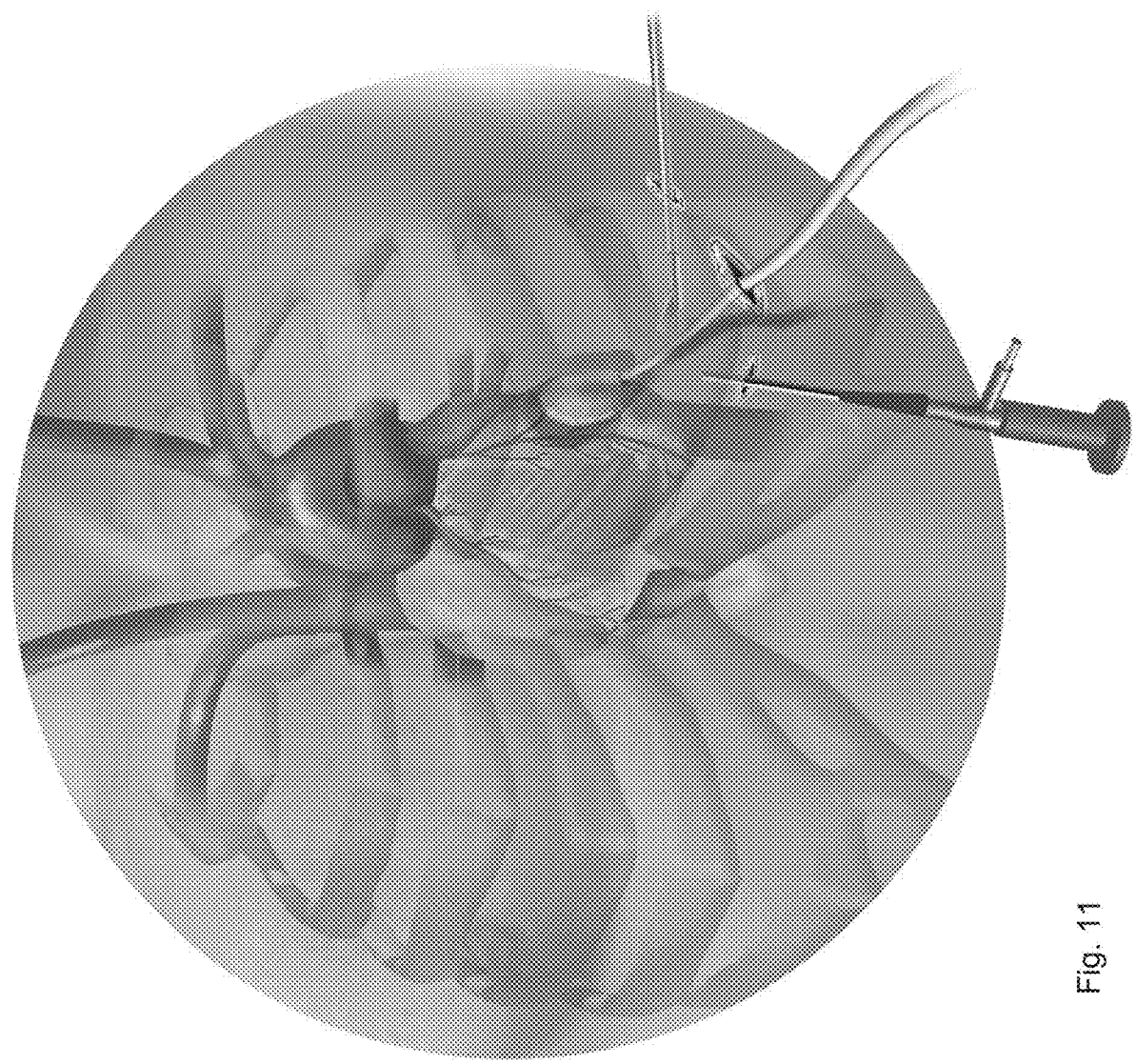
FIG. 11 illustrates placement of the assist device on an infarct of the heart using minimally invasive surgical techniques.
Figure 12:
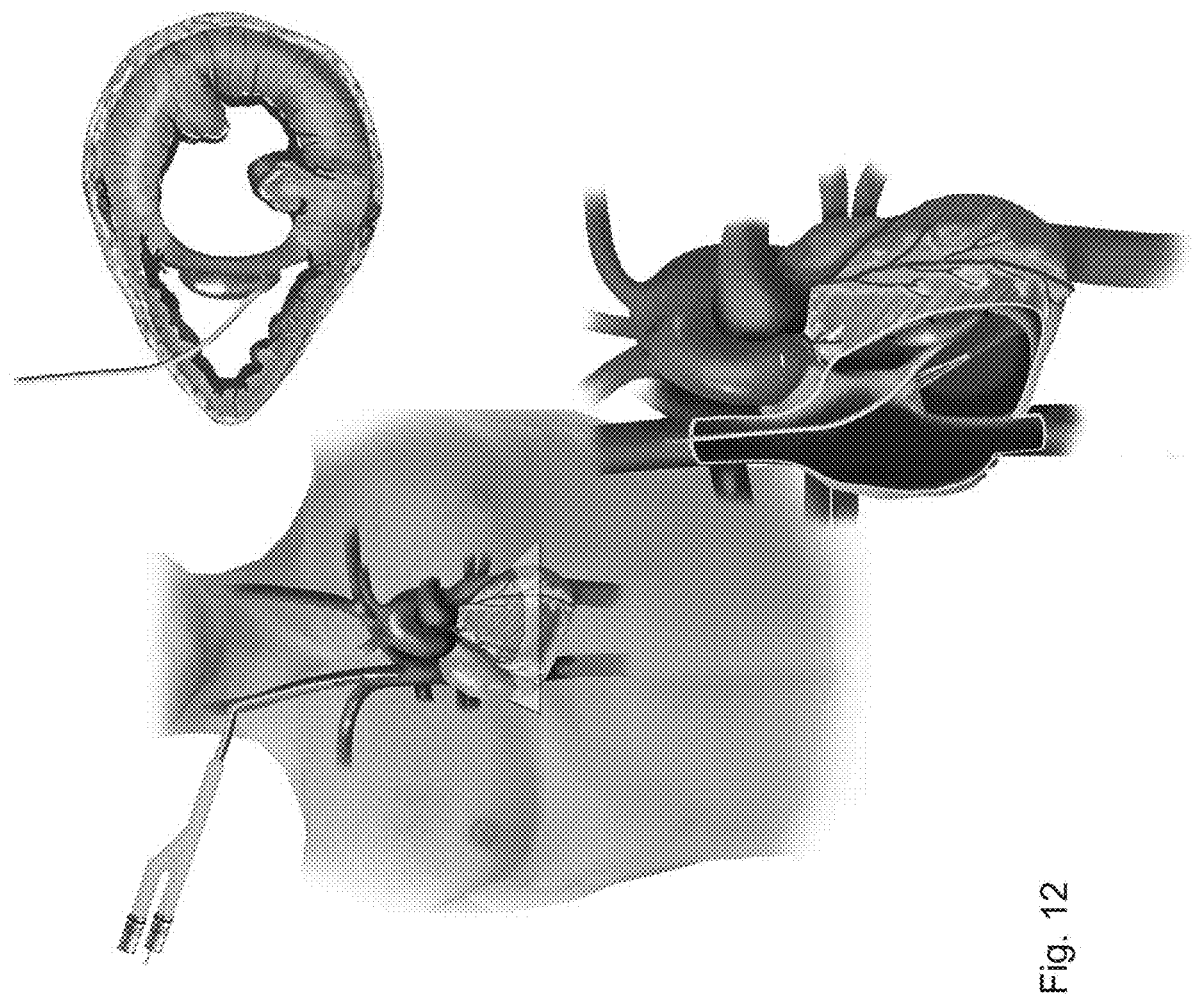
FIG. 12 illustrates placement of the assist device on an infarct of the heart using transcutaneous techniques.

A standard full sternotomy or thoracotomy could be used. This would be most likely in patients who are having concomitant valve or coronary artery surgery. On the other hand, a subxiphoid approach using a small upper abdominal incision made to expose and open the pericardium may be used as illustrated in FIG. 11. Also, a mini-thoracotomy may be used to expose and enter the pericardium. Either of these latter methods may be performed with the aid of thoracoscopic surgical technology or robotic surgical technology. As shown in FIG. 12, a purely percutaneous, transvenous approach could be used to place a restraining device in the right ventricle to stabilize a damaged intraventricular septum. On the other hand, FIG. 13 illustrates placement of an assist device on the infarct via transcutaneous techniques where the assist device is in the form of a wire mesh that is collapsed for insertion into a delivery sheath and is placed via a subxiphoid approach.

2. Heart Stabilization

Minimally invasive surgical approaches that utilize subxiphoid or mini-thoracotomy approaches could be facilitated by using heart holding or stabilizing devices that are now currently used for off-pump surgical coronary revascularization procedures. Those skilled in the art will appreciate that the assist device of the invention may be applied to the heart in an off-pump beating heart procedure or an on-pump still heart procedure.

3. Device Delivery

The uninflated or unexpanded device (bladder, balloon or nitinol mesh structure) could be placed in a thin catheter and passed through a small incision in the chest and pericardium and placed against the desired portion of the injured heart. This placement could be guided by intraoperative imaging such as fluoroscopy, echocardiography or MRI. Robotic and/or thoracoscopic techniques could be used to aid in minimally invasive delivery.

4. Device Fixation

Sutures may be used to fix the assist device 10 to the heart using standard surgical tools as well as sutures placed with thoracoscopic or robotic surgical tools. Other fixation devices include staples, bioglues, prothrombotic agents, materials that cause inflammation, combination of an intact pericardium and a long tether that is secured in the wound, and the device 10 could be incorporated into any number of surgical meshes to facilitate suturing and to encourage attachment to the myocardium.

5. Optimization

Echocardiography, MRI and or fluoroscopy may be used to optimize degree and timing of device inflation. The positioning of the device 10 and size of the device 10 could be optimized based on these imaging techniques. Also, diagnostic catheter technology (Swan-Ganz catheter) could be used to optimize the device for maximal ejection fraction, stroke volume, cardiac output, reduction in LV size at end systole, reduction in LV wall stress, reduction in regional dyskinetic LV wall motion, reduction in infarct bulging, and/or improvement in LV vortex shape and distribution.

Applications for Use of Assist Device

As will be apparent from the above description, the assist device of the invention may be used for numerous therapeutic applications. For example, the assist device has potential benefits for patients with chronic impaired LV function (with or without regional wall motion abnormalities) as well as for patients who have suffered an acute myocardial infarction (heart attack). The assist device also may limit mitral regurgitation in patients with reduced LV function and mitral regurgitation. The device also may normalize blood flow through the LV.

1. Chronic LV Impairment

The device can improve cardiac efficiency by eliminating a cavity volume of the ventricle bounded by the injured heart tissue thereby redirecting blood volume from a non-contractile injured region of the ventricle to a contractile remote region of the ventricle. This is a static modification in the heart's diastolic function to affect an improvement in systolic performance. The device also can provide active mechanical assistance to the impaired heart by coupling device inflation with the cardiac cycle. This is a dynamic modification in the heart's systolic function. These approaches also may be combined.

2. Mitral Regurgitation that Results from LV Remodeling

The device in either active or dynamic state of function can be placed on the surface of the heart to reposition the papillary muscle relative to the mitral valve annulus thereby relieving mitral valve leaflet tethering and reducing valve regurgitation. The device also can alter blood flow within the LV to improve mitral valve closure. External restraint from the device can act to normalize LV vortex formation which has been shown to affect mitral valve closure.

3. Acute Myocardial Infarction

The device can be permanently placed over the area of an acute myocardial infarction early after the MI to reduce mechanical stress in the infarct and surrounding uninfarcted regions of the heart. The reduced stress will limit LV dilatation and slow or inhibit the onset of heart failure. The device also can be placed temporarily to improve infarct healing so the infarct becomes stiffer. This is analogous to splinting a bone fracture. Also, by reducing the mechanical stress in the infarct, even temporarily, improve infarct healing can be improved and result in a stiffer infarct long-term. The mechanical means of restraint can then be removed. The stiffer infarct will prevent or reduce LV dilation and slow or eliminate the progression to heart failure.

4. Combined Uses

For all the above uses just described, the device could be an adjustable balloon or bladder that could be filled with a fluid to optimize the static and/or dynamic benefit of the device for an individual patient. The optimal degree of inflation and timing of inflation for each patient could be determined by echocardiography or MRI. Also, the balloon or bladder may be constructed to have regional variation in stiffness so as to cause the balloon or bladder to preferentially expand in the preferred direction (i.e. towards the heart) and not a non-preferred direction.

5. Static Uses

For the static (passive) uses indicated above, the device could be (in addition to adjustable balloon or bladder) a fixed solid object whose shape is customized to the patient and designed to improve cardiac efficiency by eliminating a cavity volume of the ventricle bounded by the injured heart tissue thereby redirecting blood volume from a non-contractile injured region of the ventricle to a contractile remote region of the ventricle. The shape of this device could be optimized for individual patients based on pre-operative echocardiography and MRI. Computational stress modeling of the heart could also be used to design the device's shape for individual patients. Stress modeling could be based on MRI or echocardiographic imaging. A self-expanding nitinol mesh device would be one way to do this. A solid device may also be used that is absorbable or that could be removed so as to provide infarct restraint and promote infarct healing and stiffening. It would be absorbed after stiffening was complete.

6. Optimization of LV Blood (Vortex Formation)

The assist device of the invention may also be used to improve contractile efficiency, to improve mitral valve function, and to reduce potential for thrombus formation.

Those skilled in the art will also appreciate that the invention may be applied to other applications and may be modified without departing from the scope of the invention. For example, those skilled in the art will appreciate that the device of FIG. 7 can be used in patients who suffer myocardial infarction to stiffen the infarct region in an adjustable fashion so that the infarct stiffness can be varied to optimize the results in each patient. The device may be implanted in patients without contacting the patient's blood with non-endotheilized surfaces (i.e., artificial surfaces), thereby reducing a primary cause of morbidity and death as a result of implantation of conventional devices. Those skilled in the art will further appreciate that the assist device of the invention may be used to treat either ventricle and is not limited to use in the specific applications described herein. Accordingly, the scope of the invention is not intended to be limited to the exemplary embodiments described above, but only by the appended claims.

What is claimed:

1. A mechanical assist device configured for selectively stiffening injured tissue of a ventricle, to alter ventricle geometry a desired amount, or both, comprising:
   a first fluid fill chamber configured to provide dynamic assistance to the ventricle, and for being selectively coupled to the injured tissue;
   a first fluid reservoir that is in fluid communication with the first fluid fill chamber via a first feed line for supplying a fluid to the first fluid fill chamber;
   a pulsatile device for cyclically changing the volume of fluid in the first fluid fill chamber;
   a second fluid fill chamber configured to statically stiffen the ventricle and for being selectively placed over said injured tissue in overlapping arrangement with the first fluid fill chamber; and,
   a second fluid reservoir that is in fluid communication with the second fluid fill chamber via a second feed line for adjusting the volume of the second fluid fill chamber at least by supplying a fluid to the second fluid fill chamber.

2. The mechanical assist device of claim 1, wherein the pulsatile device is configured to increase the volume of fluid in the first fluid fill chamber when the ventricle is in systole and decrease the volume of fluid in the first fluid fill chamber when the ventricle is in diastole.

3. The mechanical assist device of claim 1, further comprising a controller that is configured to control the pulsatile device by synchronizing the pulsatile device with the cardiac cycle of the ventricle.

4. The mechanical assist device of claim 1, further comprising a volume adjustment device that is configured to statically maintain the volume of fluid in the second fluid fill chamber.

5. The mechanical assist device of claim 4, wherein the volume adjustment device is further configured to vary the volume of fluid in the second fluid fill chamber over time in accordance with a desired stiffness of the injured tissue.

\* \* \* \* \*